United States Patent
Sartori et al.

(10) Patent No.: US 6,210,830 B1
(45) Date of Patent: Apr. 3, 2001

(54) LITHIUM FLUOROPHOSPHATES AND THEIR USE AS CONDUCTING SALTS

(75) Inventors: Peter Sartori, Rheinberg; Nikolai Ignatyev, Duisburg, both of (DE)

(73) Assignee: Merck Patent Gesellschaft mit beschrankter Haftung (DE)

( * ) Notice: Subject to any disclaimer, the term of this patent is extended or adjusted under 35 U.S.C. 154(b) by 0 days.

(21) Appl. No.: 09/284,010

(22) PCT Filed: Sep. 24, 1997

(86) PCT No.: PCT/EP97/05230

§ 371 Date: Mar. 8, 2000

§ 102(e) Date: Mar. 8, 2000

(87) PCT Pub. No.: WO98/15562

PCT Pub. Date: Apr. 16, 1998

(30) Foreign Application Priority Data

Oct. 5, 1996 (DE) .............................. 196 41 138

(51) Int. Cl.[7] .............................. C07F 9/28; C07F 9/535; H01M 10/08

(52) U.S. Cl. ..................... 429/199; 429/189; 429/324; 429/200; 429/203; 252/62.2; 423/301; 423/323; 423/179.5; 568/16

(58) Field of Search ................... 429/189, 324, 429/199, 200, 203; 252/62.2; 423/301, 323, 179.5; 568/16

(56) References Cited

U.S. PATENT DOCUMENTS 4,900,854 * 2/1990 Winterton et al. .................. 556/70
5,916,475 * 6/1999 Michot et al. .................. 252/62.2

FOREIGN PATENT DOCUMENTS

WO 88/03331 * 5/1988 (WO).
WO 94/27335 * 11/1994 (WO).

OTHER PUBLICATIONS

Muetterties et al, Inorganic Chemistry, vol. 3, No. 9, pp. 1298–1303, Sep. 1964.*
Oberhammer et al, Inorganic Chemistry, vol. 21, No. 1, pp. 275–281, 1982 (month unknown).*
Pavlenko et al, Journal of General Chemistry, USSR, vol. 59, No. 3, pp. 469–473, Aug. 1989.*
Kampa et al., Angewandte Chemie, vil. 34, No. 11, pp. 1241–1244, Jun. 1995.*
Ignat'ev et al, Journal of Fluorine Chemistry, vol. 101, pp. 203–207, 2000 (month unknown).*

(List continued on next page.)

*Primary Examiner*—Alan Diamond
(74) *Attorney, Agent, or Firm*—Millen, White, Zelano & Branigan, P.C.

(57) ABSTRACT

The invention relates to novel lithium fluorophosphates of the general formula $$Li^+[PF_a(CH_bF_c(CF_3)_d)_e]^-, \quad (I)$$

Figure 1:
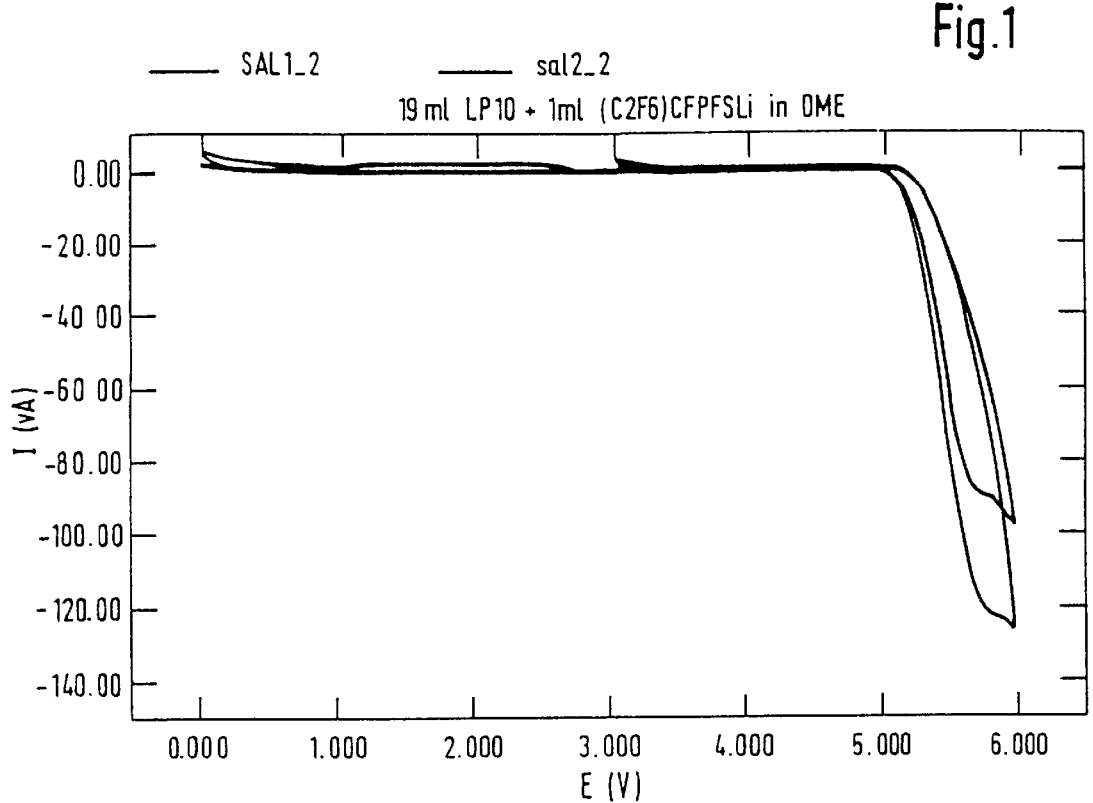

wherein
 a is 1, 2, 3, 4 or 5,
 b is 0 or 1,
 c is 0, 1, 2 or 3,
 d is 0, 1, 2 or 3 and
 e is 1, 2, 3 or 4,
with the condition that the sum of a+e is equal to 6, the sum of b+c+d is equal to 3 and b and c are not simultaneously 0, with the proviso that the ligands $(CH_bF_c(CF_3)_d)$ may be different,
a process for producing said compounds, their use in electrolytes, and also lithium batteries produced using said electrolytes.

13 Claims, 1 Drawing Sheet

OTHER PUBLICATIONS

Ignat'ev et al, Journal of Fluorine Chemistry, vol. 103, pp. 57–61, 2000 (month unknown).*

E.L. Muetterties et al., *Inorganic Chemistry*, vol. 3, No. 9, pp. 1298–1303, Sep. 1964.

H. Oberhammer, *Inorganic Chemistry*, vol. 21, No. 1 (1982), pp. 275–281 (month unknown).

N.V. Pavlenko et al., *Journal of General Chemistry USSR*, vol. 59, No. 3, pp. 469–473, Aug. 1989.

* cited by examiner

LITHIUM FLUOROPHOSPHATES AND THEIR USE AS CONDUCTING SALTS

The invention relates to novel lithium fluorophosphates of the general formula $$Li^+[PF_a(CH_bF_c(CF_3)_d)_e]^-, \quad (I)$$

wherein
a is 1, 2, 3, 4 or 5,
b is 0 or 1,
c is 0, 1, 2 or 3,
d is 0, 1, 2 or 3 and
e is 1, 2, 3 or 4,
with the condition that the sum of a+e is equal to 6, the sum of b+c+d is equal to 3 and b and c are not simultaneously 0, with the proviso that the ligands $(CH_bF_c(CF_3)_d)$ may be different,
a method for producing said compounds,
their use in electrolytes, and also lithium batteries produced with said electrolytes.

The invention also relates to compounds of the general formula $$[PF_a(CH_bF_c(CF_3)_d)_e] \quad (Ia),$$

wherein, as in formula (I),
b is 0 or 1,
c is 0, 1, 2 or 3,
d is 0, 1, 2 or 3 and
e is 1, 2, 3 or 4,
but
a is 1, 2, 3 or 4,
which are needed as intermediates for producing compounds of the formula (I).

Normally, lithium hexafluorophosphate is used as conducting salt in lithium secondary batteries. A disadvantage is that this salt has relatively little resistance to hydrolysis. Various experiments were therefore performed to find a replacement for said salt. For example, WO 88/03331 describes salts of cyclic perfluoroalkanebis(sulphonyl) imides, including also their lithium salts, which can be used as conducting salts in nonaqueous electrolytes for lithium secondary batteries. As experiments have revealed, such compounds can, however, be produced only at great expense and have to be freed from undesirable byproducts after the synthesis. The purification of the salts is indispensable since reproducible properties are indispensable for application as constituents of battery electrolytes.

The object of the invention is therefore to provide suitable conducting salts for electrolytes for use in lithium batteries. The object of the invention is also to provide a process by which the conducting salts according to the invention can be produced easily and inexpensively.

The object according to the invention is achieved by novel lithium fluorophosphates of the general formula $$Li^+[PF_a(CH_bF_c(CF_3)_d)_e]^-, \quad (I),$$

wherein
a is 1, 2, 3, 4 or 5,
b is 0 or 1,
c is 0, 1, 2 or 3,
d is 0, 1, 2 or 3 and
e is 1, 2, 3 or 4,
with the condition that the sum a+e is equal to 6, the sum b+c+d is equal to 3 and b and c are not simultaneously 0 and with the condition that the ligands $(CH_bF_c(CF_3)_d)$ may be different,
which lithium fluorophosphates can replace the lithium hexafluorophosphate conventionally used as conducting salt in lithium secondary batteries, and can also be used as a mixture with the latter.

The invention therefore relates to the novel salts according to the invention of the formula (I) and also to a process for producing them and compounds of the general formula (Ia), $$[PF_a(CH_bF_c(CF_3)_d)_e] \quad (Ia),$$

wherein, as in formula (I)
b is 0 or 1,
c is 0, 1, 2 or 3,
d is 0, 1, 2 or 3 and
e is 1, 2, 3 or 4,
but
a is 1, 2, 3 or 4,
which are needed as intermediates for producing the salts in accordance with the general formula (I).

Finally, the invention also relates to electrolytes which comprise the salts according to the invention and electrochemical cells produced using said electrolytes. Such electrochemical cells can be either primary or secondary batteries which comprise the lithium compounds according to formula (I).

The invention relates, in particular, to the following lithium salts a)

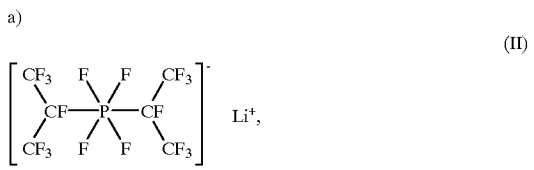
(II)

b)

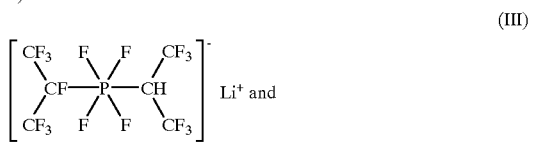
(III)

c)

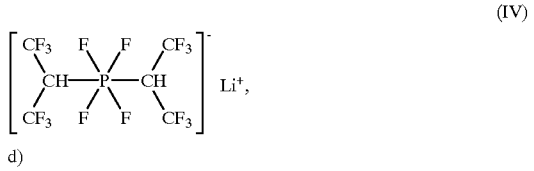
(IV)

d)

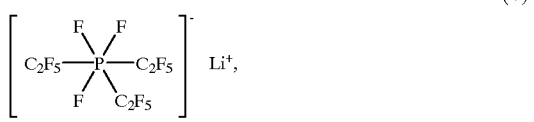
(V)

e)

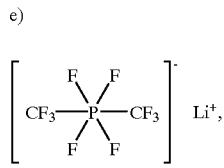 (VI)

f)

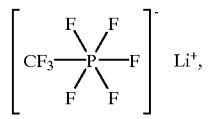 (VII)

g)

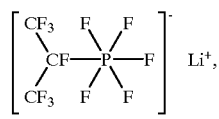 (VII)

h)

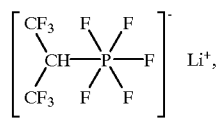 (IX)

their use as conducting salts in electrolytes, electrolytes comprising them, and also lithium batteries in which said compounds are comprised as conducting salts.

To produce the salts according to the invention, in a first step, suitable monochloro- or fluoro-, dichloro- or difluoro-, chlorofluoroalkylphosphanes, chloromono-, chlorodi-, chlorotri-, or chlorotetraalkylphosphoranes, fluoromono-, fluorodi-, fluorotri- or fluorotetraalkylphosphoranes or trifluoromonohydroalkylphosphoranes are taken up in a solvent and electrochemically fluorinated in a known manner at a temperature of −15 to 20° C. under normal pressure. Hydrogen fluoride is suitable as a solvent for this reaction. The fluorination reaction is terminated when 90 to 150%, in particular 110 to 130%, of the theoretical quantity of electricity has been consumed. This is determined by coulometric measurement.

Depending on the duration of the reaction, product mixtures are obtained which comprise both compounds completely saturated with fluorine and those which are partially fluorinated. For example, the following products are obtained in the fluorination of chlorodiisopropylphosphane:

a)

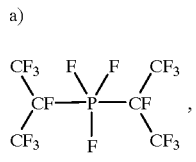 (IIa)

b)

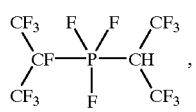 (IIb)

c)

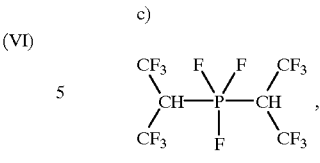 (IIc)

d)

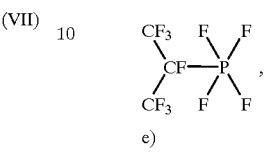 (IId)

e)

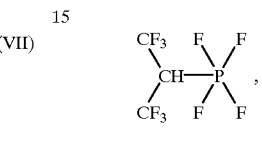 (IIe)

The actual salts according to the invention of the formula (I) are obtained by the fluorinated alkylphosphoranes (II) obtained in the first stage being taken up as a product mixture, preferably after distillative separation, under anhydrous conditions in a suitable aprotic, polar solvent, such as, for example, dimethyl ether, dimethoxyethanes or their mixtures and reacted with lithium fluoride to form compounds of the formula (I), depending on reactivity, at a temperature of −35 to 60° C., preferably adhering to room temperature.

In the electrolytes according to the invention, both the pure compounds of the formula (I) and the mixtures obtained by the fluorination reaction can be used. Preferably, the pure compounds are used to produce the electrolyte solutions because of the reproducibility of the electrolyte properties.

Surprisingly, it was found by experiments that compounds of the formula (I) are resistant to hydrolysis in aprotic polar solvents at room temperature and, to be specific, those compounds, in particular, whose alkyl radicals are completely saturated with fluorine. In this connection, the resistance to hydrolysis increases with the number of fluorine atoms in the molecule.

Aprotic polar solvents are to be understood as meaning solvents such as

| | |
|---|---|
| nitriles | acetonitrile or benzonitrile, |
| ethers | diethyl ether, dimethoxyethane, tetrahydrofuran, dioxane or dimethyltetrahydrofuran, |
| esters | methyl or ethyl esters of formic acid, acetic acid, propionic acid, and also cyclic esters, such as butyrolactone, and organic carbonates, such as, for example, dimethyl carbonate, diethyl carbonate, ethyl methyl carbonate, ethylene carbonate or propylene carbonate, |
| amides | dimethylformamide, diethylformamide, N-methylpyrolidine |
| or | |
| sulphones | dimethyl sulphone, tetramethylene sulphone or other sulpholanes. |

The salts according to the invention have, in addition, an excellent solubility in said solvents and, in particular, the compounds completely saturated with fluorine have little hygroscopy.

Experiments have shown that these compounds are extremely stable. With dry storage in the solid state, perfluorinated compounds exhibit no decomposition at temperatures below 100° C. They prove to be thermally table even on increasing the temperature further. It is only at temperatures above 130° C. that they exhibit slight discolorations.

Even on storage in solution, for example in dimethoxyethane, no colour changes can be observed or decomposition products detected even after weeks.

For this reason, the compounds according to the invention, in particular the compounds of the formulae III, IV, V, VI and VII, are already excellently suited as conducting salts in nonaqueous electrolytes for lithium batteries.

Furthermore, electrolyte solutions which contain these compounds have remarkable chemical and electrochemical stability. In particular, oxidation of the corresponding anion cannot be detected prior to the lithium deposition.

Such electrolytes comprise, in addition to organolithium salts, such as the compounds according to the invention of the formula (I) one or more nonaqueous organic solvents and, optionally, further additives. If desired, in addition to the compounds according to the invention, already known lithium salts can also be added to the electrolyte as conducting salts. Further details on such electrolytes and the structure or mode of operation of lithium batteries are known to the person skilled in this field of technology. The compounds according to the invention can be used completely analogously to lithium compounds known for this application and, under these conditions, exhibit extremely high stabilities. Corresponding battery cells exhibit excellent properties in relation to capacity and constant voltage and also an unlimited serviceability over an above-average large number of charge-discharge cycles.

BACKGROUND OF THE INVENTION

Figure 2:
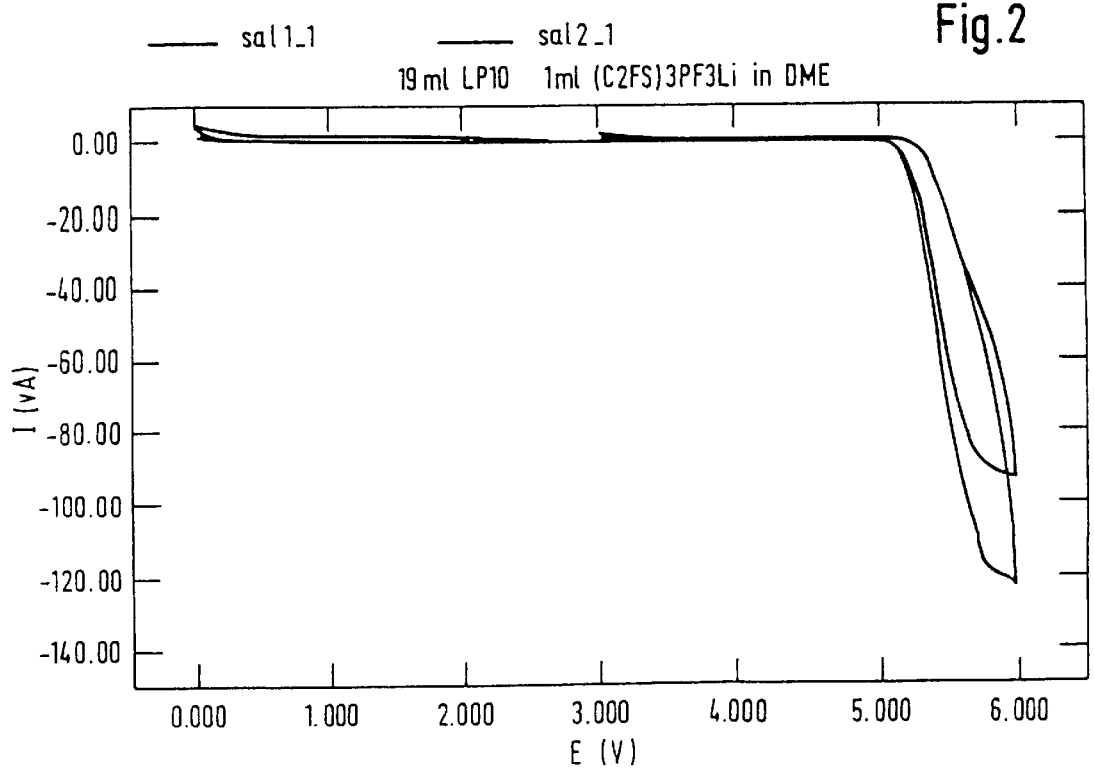

FIGS. 1 and 2 represent data generated in cycling experiments with various lithium salts, as detailed in Examples 4 and 5.

The examples given below are given to provide a better illustration of the present invention, but are not designed to limit the invention to the features disclosed herein.

EXAMPLES

Example 1

Bis(heptafluoroisopropyl)trifluorophosphorane (IIa) and its derivatives

Diisopropylchlorophosphane is electrochemically fluorinated by the Simons process in an electrochemical cell which comprises hydrogen fluoride as solvent. The cylindrical cell used having a volume of 310 cm$^3$ is fitted with nickel anodes having an effective surface area of S=3.75 dm$^2$ and cathodes having the same effective surface area. Furthermore, the cell is fitted with a cooling condenser. The cell temperature is kept at −5° C. during the electrolysis and the condenser at −30° C.

57 g of diisopropylchlorophosphane dissolved in 200 g of hydrofluoric acid are added in portions to 235 g of previously electrolysed hydrofluoric acid, and to be specific, in the following way:

| Electrolysis time [A h] | Amount of diisopropylchlorophosphane [g] |
|---|---|
| 0 | 10 |
| 78.1 | 10 |
| 157.4 | 10 |
| 230.6 | 10 |
| 294.0 | 10 |
| 365.2 | 7 |

Gaseous products which have passed through the cooling condenser and two PTFE traps are cooled to −78° C.

The electrolysis, which is performed at a voltage of 4.4–5.4 V and a current density of 0.30–0.53 A/dm$^2$ is terminated after a current consumption of 420 A h (131% of theory), about 220 g of liquid product being collected from the cell. After the temperature has been adjusted to −20° C. and the lower phase had been separated off from the hydrogen fluoride phase, 18 g of raw product are obtained. 75% of bis(heptafluoroisopropyl)trifluorophosphorane (IIa), 15% of heptafluoroisopropyl(1,1,1,3,3,3-hexafluoroisopropyl)trifluorophosphorane (IIb) and bis(hex-1,1,1,3,3,3-hexafluoroisopropyl)trifluorophosphorane (IIc) can be detected therein by NMR $^{19}$F spectroscopy.

This mixture can be separated by fractional distillation into fractions which each comprise one of these compounds as main component. In addition, after the separation of the hydrogen fluoride phase, 33 g of products which are liquid at low temperatures are obtained from the cooling traps. Investigations by NMR $^{19}$F spectroscopy show that these are predominantly heptafluoroisopropyltetrafluorophosphorane (IId), 1,1,1,3,3,3-hexafluoroisopropyltetrafluorophosphorane (IIe) and perfluoropropane. The perfluoropropane can be distilled off by heating to 20° C. The residue can be separated by fractional distillation into fractions which comprise heptafluoroisopropyltetrafluorophosphorane (IId) or 1,1,1,3,3,3-hexafluoroisopropyltetrafluorophosphoranes (IIe) as main components.

The compounds obtained can be characterized by the following data:

Bis(heptafluoroisopropyl)trifluorophosphorane (IIa)

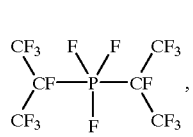

(IIa)

NMR $^{19}$F, ppm: (CD$_3$CN film with CCl$_3$F as standard)
−39.72 dtm (3 F$^1$)
−70.15 m (12 F$^3$)
−171.78 dm (2 F$^2$)
J$^3_{F^1F^2}$=8.0 Hz
NMR $^{31}$P, ppm: (CD$_3$CN film with 85% H$_3$PO$_4$ as standard)
−26.0 qtm
J$^1_{P,F^1}$=1083 Hz
J$^2_{P,F^2}$=102 Hz
J$^3_{P,F^3}$=4.9 Hz
Heptafluoroisopropyl(1,1,1,3,3,3-hexafluoroisopropyl)trifluorophosphorane (IIb)

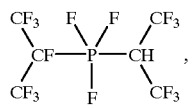
(IIb)

NMR $^{19}$F, ppm: (CD$_3$CN film with 85% CCl$_3$F as standard)
-33.10 dm (3 F$^1$)
-59.56 m (6 F4)
-70.26 m (6 F$^3$)
-171.90 m (1F$^2$)
NMR $^{31}$P, ppm: (CD$_3$CN film with 85% H$_3$PO$_4$ as standard)
-23.2 qdm
J$^1_{P,F^1}$=1014.0 Hz
J$^2_{P,F^2}$=99.0 Hz
J$^3_{P,F^3}$=5.2 Hz
J$^3_{P,F^4}$=5.7 Hz
J$^2_{P,H}$=11.0 Hz
NMR $^1$H, ppm: (CD$_3$CN film with TMS as standard)
3.9 dm
Bis(hexa-1,1,1,3,3,3-hexafluoroisopropyl)trifluorophosphorane (IIc)

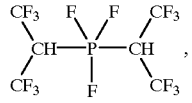
(IIc)

NMR $^{19}$F, ppm: (CD$_3$CN film with CCl$_3$F as standard)
-25.96 dm (3 F$^1$)
-59.51 m (12 F$^2$)
NMR $^{31}$P, ppm: (CD$_3$CN film with 85% H$_3$PO$_4$ as standard)
-20.69 qm
J$^1_{P,F^1}$=960.0 Hz
J$^3_{P,F^2}$=11.3 Hz
NMR $^1$H, ppm: (CD$_3$CN film with TMS as standard)
3.9 dm
Heptafluoroisopropyltetrafluorophosphorane (IId)

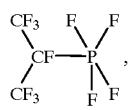
(IId)

NMR $^{19}$F, ppm ((CD$_3$CN film with CCl$_3$F as standard); -30° C.):
-50.10 dm (4 F$^1$)
-72.22 m (6 F$^3$)
-172.83 dm (1 F$^2$)
NMR $^{31}$P, ppm ((CD$_3$COCD$_3$ film with 85% H$_3$PO$_4$ as standard); -40° C.):
-55.3 pdsep
J$^1_{P,F^1}$=1042.0 Hz
J$^2_{P,F^2}$=100.0 Hz
J$^3_{P,F^3}$=6.0 Hz 1,1,1,3,3,3-Hexafluoroisopropyltetrafluorophosphorane (IIe)

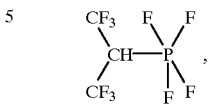
(IIe)

NMR $^{19}$F, ppm ((CD$_3$CN film with CCl$_3$F as standard); -30° C.):
-40.90 dm (4 F$^1$)
-61.8 m (6 F$^2$)
NMR $^{31}$P, ppm (CD$_3$COCD$_3$ film with 85% H$_3$PO$_4$ as standard -40° C.):
-50.8 pdsep
J$^1_{P,F^1}$=1003.0 Hz
J$^3_{P,F^2}$=14.0 Hz
J$^2_{P,H}$=27.0 Hz Example 2
Tris(pentafluoroethyl)difluorophosphorane (Va)

70 g of tris(pentafluoroethyl)difluorophosphorane (Va) are prepared analogously to the procedure described in Example 1 from 69 g of triethylphosphine oxide. NMR $^{31}$P spectroscopic data agree with those in the literature (V. J. Semenii et al.; Zh. Obshch. Khim. (Russ.) 1985, Vol. 55, 12, 2716–2720):

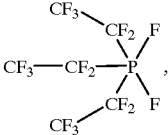
(Va)

NMR $^{31}$P, (CD$_3$COCD$_3$ film with 85% H$_3$PO$_4$ as standard), ppm:
-47.55 tsep
J$^1_{P,F}$=1003.0 Hz
J$^2_{P,F}$=122.0 Hz Example 3
Lithium bis(heptafluoroisopropyl)tetrafluorophosphate (II)

12 g (0.028 mol) of bis(heptafluoroisopropyl)trifluorophosphorane (IIa) are slowly added while stirring with a magnetic stirrer with moisture excluded to a solution contained in a PTFE reaction vessel consisting of 0.82 g (0.031 mol) of LiF and 60 ml of predried dimethoxyethane, the temperature being kept at room temperature by cooling in an ice-water bath. Stirring is then carried out at the same temperature for one hour and small amounts of metallic lithium are also added. The reaction mixture is kept at room temperature for 24 h, then filtered and can be used immediately as an electrolyte for rechargeable batteries. The lithium bis(heptafluoroisopropyl)tetrafluorophosphate (II) formed during the reaction can, however, also be isolated by distilling off the solvent under high vacuum.

A lithium complex salt (II), Li$^+$[i-C$_3$F$_7$)$_2$PF$_4$]$^-$×2 DME is isolated, m.p.: 126–128°; thermally stable up to 130° C.

Analysis: Li
theoretical: 0.93%
actual: 1.15%

The solvent can be removed by heating the complex salt (II) in high vacuum for several days at a temperature of 80° C.

Example 3a

To produce lithium salts according to the invention, the fluorophosphorane mixture obtained in Example 1 can be used directly without previous fractional distillation.

16 g of a fluorophosphorane mixture from Example 1 comprising 75% of the compound (IIa), 15% of the compound (IIb) and 10% of the compound (IIc) were added, as described above, to a solution consisting of 1.0 g of LiF and 80 ml of dry DME. This solution can also be used directly as electrolyte after filtering. The Li salts may, however, also crystallize out of the solution if predried hexane is added to the DME solution. 13.6 g of lithium bis(heptafluoroisopropyl)tetrafluorophosphate (II), together with 6% lithium heptafluoroisopropyl(1,1,1,3,3,3-hexafluoroisopropyl)tetrafluorophosphate (IV), are obtained by recrystallizing the product obtained with a solvent mixture consisting of dried DME and dibutylether (1:2).

The structure of the salts (II) and (III) was detected by NMR $^{19}$F and $^{31}$P spectroscopy. NMR spectra were measured in $CD_3COCD_3$ solutions with $CCl_3F$ and, if not, 85% $H_3PO_4$ as external standards.

Lithium bis(heptafluoroisopropyl)tetrafluorophosphate (III)
NMR $^{19}$F, ppm:
 −58.14 dm (4 $F^1$)
 −71.07 pdd (12 $F^3$)
 −184.40 dpsep (2 $F^2$)
 $J^3_{F^1,F^2}$=4.0 Hz
 $J^4_{F^1,F^3}$=10.9 Hz
 $J^3_{F^2,F^3}$=4.7 Hz
NMR $^{31}$P, ppm:
 −149.27 ptm
 −148.42 ptm ($CD_3CN$ solution)
 $J^1_{P,F^1}$=943.0 Hz
 $J^2_{P,F^2}$=75.0 Hz
 $J^3_{P,F^3}$=8.2 Hz Lithium heptafluoroisopropyl(1,1,1,3,3,3-hexafluoroisopropyl)tetrafluorophosphate (IV)
NMR $^{19}$F, ppm:
 −47.20 dddm (4 $F^1$)
 −58.01 dpd (6 $F^4$)
 −70.79 pdd (6 $F^3$)
 −183.50 dm (1 $F^2$)
 $J^3_{F^1,F^2}$=4.1 Hz
 $J^3_{H,F^1}$=4.1 Hz
 $J^3_{F^2,F^3}$=8.0 Hz
 $J^4_{F^1,F^3}$=11.5 Hz
 $J^4_{F^1,F^4}$=11.5 Hz
NMR $^{31}$P, ppm:
 −147.37 pdm
 $J^1_{P,F^1}$=928.0 Hz
 $J^2_{P,F^2}$=74.5 Hz
 $J^3_{P,F^3}$=8.3 Hz
 $J^3_{P,F^4}$=11.4 Hz

Example 4

Lithium heptafluoroisopropylpentafluorophosphate (VIII)

Lithium heptafluoroisopropylpentafluorophosphate (VIII) is obtained in an analogous way to that described in Example 3 by reacting fluorophosphorane (IId) with LiF in dry dimethoxyethane. As described, the solution obtained after filtering can be used directly as electrolyte solution or the abovementioned salt can be isolated by distilling off the solvent under high vacuum or by crystallization resulting from adding hexane.

The mixture of fluorophosphoranes obtained according to Example 1 can also be used to produce electrolyte solutions by reacting them with LiF without prior purification. The solution of the two lithium salts (VIII) and (IX) which is obtained in this case can also be used as electrolyte for lithium batteries.

Both salts can be isolated in the same way as described above.

Lithium heptafluoroisopropylpentafluorophosphate (VIII)
NMR $^{19}$F, ppm: (solvent: $CD_3COCD_3$; standard: $CCl_3F$)
 −62.62 dddsep (4 $F^1$)
 −73.13 p (1 $F^2$)
 −71.49 pdd (6 $F^4$)
 −183.72 dpsepm (1 $F^3$)
 $J^2_{F^1,F^2}$=45.4 Hz
 $J^3_{F^1,F^3}$=3.6 Hz
 $J^3_{F^3,F^4}$=4.2 Hz
 $J^4_{F^1,F^4}$=11.4 Hz
NMR $^{31}$P, ppm: (solvent: $CD_3CN$; external standard: 85% $H_3PO_4$)
 −148.16 pddsep
 $J^1_{P,F^1}$=841.0 Hz
 $J^1_{P,F^2}$=717.0 Hz
 $J^2_{P,F^3}$=68.7 Hz
 $J^3_{P,F^4}$=4.9 Hz Lithium 1,1,1,3,3,3-hexafluoroisopropylpentafluorophosphate (IX)
NMR $^{19}$F, ppm: (solvent: $CD_3COCD_3$; standard: $CCl_3F$)
 −52.95 dddsep (4 $F^1$)
 −69.04 p (1 $F^2$)
 −59.40 dp (6 $F^3$)
 $J^2_{F^1,F^2}$=42.6 Hz
 $J^3_{F^1,H}$=3.8 Hz
 $J^4_{F^1,F^3}$=12.3 Hz
NMR $^{31}$P, ppm: (solvent: $CD_3CN$; external standard: 85% $H_3PO_4$)
 −145.82 pddsep
 $J^1_{P,F^1}$=829.0 Hz
 $J^1_{P,F^2}$=708.0 Hz
 $J^2_{P,H}$=29.0 Hz
 $J^3_{P,F^3}$=12.9 Hz Cycling experiments were performed using lithium heptafluoropropylpentafluorophosphate (VIII), giving the results shown in FIG. 1. These experiments were performed under the following conditions:

| | |
|---|---|
| Potential interval: | 0.0–3.0 V; 3.0–6.0 V |
| Rate of change: | 100 mV/s |
| Working electrode: | Pt, surface area $1.96 \cdot 10^3$ $cm^2$ |
| Reference electrode: | Li |
| Test electrode: | Li |
| Electrochemical stability: | up to 5.0 V |

Example 5

Lithium tris(pentafluoroethyl)trifluorophosphate (V)

Lithium tris(pentafluoroethyl)trifluorophosphonate (V) is obtained analogously to Example 3 by reaction of the corresponding fluorophosphorane (Va) obtained analogously to Example 2 with LiF in predried dimethoxyethane.

In this case, too, the reaction solution obtained after the reaction and filtration can be used directly as electrolyte or the salt (V) can be isolated by distilling off the solvent under high vacuum or by crystallization resulting from adding hexane.

Lithium tris(pentafluoroethyl)trifluorophosphate (V)

NMR $^{19}$F, ppm: (solvent: $CD_3COCD_3$; standard: $CCl_3F$)

-87.0 d (2 F$^1$)

-43.6 dm (1 F$^2$)

-115.3 m (4 F$^3$)

-115.7 m (2 F$^5$)

-79.7 m (3 F$^6$)

-81.3 m (6 F$^4$)

NMR $^{31}$P, ppm: (solvent: $CD_3COCD_3$; external standard: 85% $H_3PO_4$)

-149.8 tdpt $J^1_{P,F^1}$=902.0 Hz $J^1_{P,F^2}$=889.0 Hz $J^2_{P,F^3}$=98.0 Hz $J^2_{P,F^5}$=83.0 Hz Lithium tris(pentafluoroethyl)trifluorophosphate complex with DME (V) has a m.p. of 116–118° C. and is thermally stable up to 130° C.

FIG. 2: Cycling experiments were performed using 1 ml of lithium tris(pentafluoroethyl)trifluorophosphate (V) dissolved in DME with 19 ml of LP10 added. Results of the first and of the fifth cycling experiment are shown in FIG. 2. These experiments were performed under the following conditions:

| Potential interval: | 0.0–3.0 V; 3.0–6.0 V |
|---|---|
| Rate of change: | 100 mV/s |
| Working electrode: | Pt, surface area 1.96 E$^{-3}$ cm$^2$ |
| Reference electrode: | Li |
| Test electrode: | Li |
| Electrochemical stability: | up to 5 V |

What is claimed is:

1. A lithium fluorophosphate of formula

(I)

wherein a is 1, 2, 3, 4 or 5, b is 0 or 1, c is 0, 1, 2 or 3, d is 0, 1, 2 or 3 and e is 1, 2, 3 or 4, with the condition that the sum of a+e is equal to 6, the sum of b+c+d is equal to 3 and b and c are not simultaneously 0, with the proviso that the ligands $(CH_bF_c(CF_3)_d)$ are independently defined.

2. A lithium fluorophosphate according to claim 1 of formula a)
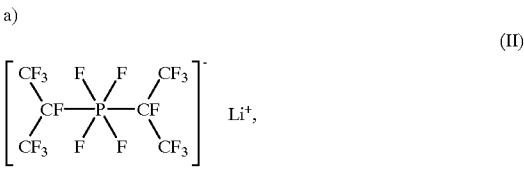
(II)

b)
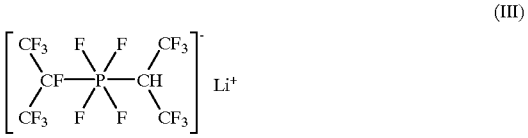
(III)

c)
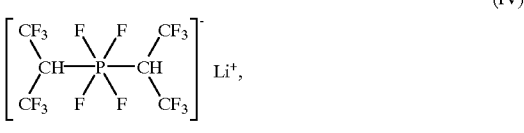
(IV)

d)
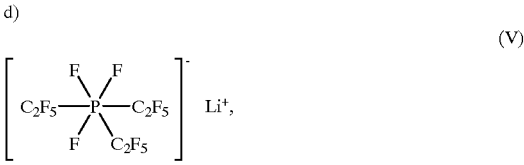
(V)

e)
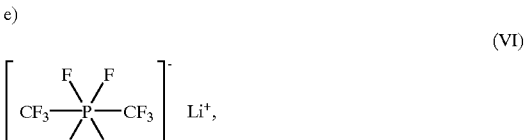
(VI)

f)
(VII)

g)
(VIII)

h)
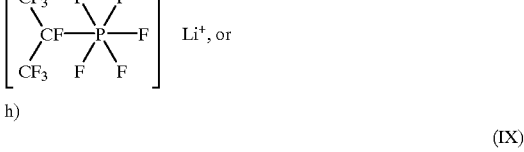
(IX)

3. Electrolytes for lithium batteries, comprising lithium fluorophosphates of the general formula (I) according to claim 1.

4. Secondary lithium batteries, comprising electrolytes according to claim 3.

5. A lithium battery containing a conducting salt, wherein the salt is a lithium fluorophosphate according to claim 1.

6. An electrolyte for an electrochemical cell comprising a lithium fluorophosphate according to claim 1.

7. An electrochemical cell comprising an electrolyte according to claim 6.

8. A process for producing lithium fluorophosphates of the formula $$Li^+[PF_a(CH_bF_c(CF_3)_d)_e]^-, \quad (I)$$

wherein
- a is 1, 2, 3, 4 or 5,
- b is 0 or 1,
- c is 0, 1, 2 or 3,
- d is 0, 1, 2 or 3, and
- e is 1, 2, 3 or 4, with the condition that the sum of a+e is equal to 6, the sum of b+c+d is equal to 3 and b and c are not simultaneously 0, with the proviso that the ligands $(CH_bF_c(CF_3)_d)$ are independently defined, wherein
- a) monochloro- or fluoro-, dichloro- or difluoro-, chlorofluoroalkylphosphines, chloromono-, chlorodi-, chlorotri- or chlorotetraalkyl-phosphoranes, fluoromono-, fluorodi-, fluorotri- or fluorotetraalkylphosphoranes or trifluoromonohydroalkyl phosphoranes are fluorinated electrochemically in an inert solvent,
- b) a fluorinated product mixture obtained is separated into different isomeric fluorination alkylphosphine products optionally by distillation and
- c) separated fluorinated alkylphosphines are reacted in an aprotic, polar solvent with lithium fluoride at a temperature of −35 to 60° C.

9. A process according to claim 8, wherein the fluorination is performed at −20° C. to room temperature and normal pressure.

10. A process according to claim 8, wherein distillative purification of the isomeric fluorination products is carried out under inert gas atmosphere.

11. A process according to claim 8, wherein reaction with lithium fluoride is carried out at room temperature.

12. A process for the preparation of a lithium fluorophosphate according to claim 1, comprising reacting a compound of formula $$[PF_a(CH_bF_c(CF_3)_d)_e] \quad (Ia),$$

wherein, as in formula (I),
- b is 0 or 1,
- c is 0, 1, 2 or 3,
- d is 0, 1, 2 or 3 and
- e is 1, 2, 3 or 4, but
- a is 1, 2, 3 or 4, with lithium fluoride.

13. A process according to claim 12, wherein the compound of formula I is produced by subjecting a monochloro- or fluoro-, dichloro- or difluoro-, chlorofluoroalkylphosphine, chloromono-, chlorodi-, chlorotri-, or chlorotetraalkylphosphorane, fluoromono-, fluorodi-, fluorotri- or fluorotetraalkylphosphorane or trifluoromonohydroalkylphosphorane to electrochemical fluorination to form a fluorinated alkyl phosphorane.

* * * * *